US00PP31793P3

(12) United States Plant Patent
Brazelton et al.

(10) Patent No.: US PP31,793 P3
(45) Date of Patent: May 26, 2020

(54) BLUEBERRY PLANT NAMED 'FC13-083'

(50) Latin Name: *Vaccinium corymbosum*
Varietal Denomination: FC13-083

(71) Applicant: Fall Creek Farm & Nursery, Inc., Lowell, OR (US)

(72) Inventors: David M. Brazelton, Walterville, OR (US); Adam L. Wagner, Eugene, OR (US); Wendy Light, Eugene, OR (US); Peter Stefan Boches, Hilo, HI (US)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 0 days.

(21) Appl. No.: 16/350,903

(22) Filed: Jan. 30, 2019

(65) Prior Publication Data

US 2019/0239406 P1 Aug. 1, 2019

Related U.S. Application Data

(60) Provisional application No. 62/709,841, filed on Jan. 31, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt

(57) ABSTRACT

The new blueberry plant variety 'FC13-083' is provided. 'FC13-083' is a commercial variety intended for the hand harvest fresh fruit market. The variety is produced from a cross of 'ZF06-050' (female parent, not patented) and 'ZF06-013' (male parent, not patented), which can be distinguished by its outstanding features.

6 Drawing Sheets

Latin name of the genus and species: *Vaccinium corymbosum.*

Variety denomination: The new blueberry plant claimed is of the variety denominated 'FC13-083'.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry (*Vaccinium corymbosum* L. hybrid) plant, referred to as 'FC13-083', as herein described and illustrated. The new blueberry plant variety 'FC13-083' is a commercial variety intended for the hand harvest fresh fruit market. The variety has moderate plant vigor, upright growth habit, ripens early to mid-season, and produces very large, uniform fruit. 'FC13-083' was selected for its above average fruit quality across all criteria. The fruit is very firm with a characteristic crunch, which is maintained during long-term cold storage. In the northern high chill blueberry market there are no cultivars in the same season that yield such large and crisp fruit as 'FC13-083', which makes it an ideal candidate for the commercial blueberry industry.

'FC13-083' has a more upright growth habit and crisper fruit compared to the parents 'ZF06-050' (not patented) and 'ZF06-013' (not patented) that have a semi-sprawling growth habit and soft fruit. 'FC13-083' differs from the female parent 'ZF06-050' (not patented) in that it has moderate vigor where 'ZF06-050' has low vigor. 'FC13-083' differs from the male parent 'ZF06-013' in that it has a higher yield, larger fruit, and an earlier season.

Pedigree and History: The new blueberry plant originated from a cross of 'ZF06-050' and 'ZF06-013' made in Lowell, Oreg., USA in 2010 and was selected in the same location in 2013.

The new blueberry variety 'FC13-083' was initially propagated by softwood cuttings in 2013 from the original seedling in Lowell, Oreg., USA and planted in a replicated plot of nine plants in fall 2014. Additional replicated plots were established in Washington, USA in 2016 and Italy in 2017. The plants established in Oregon were successfully used to establish in vitro culture lines in 2014 and plants derived from the in vitro cultures were used to establish additional replicated plots for observation and yield data collection in Oregon and Washington, USA in 2017.

'FC13-083' was selected in 2013 because of its high-quality fruit—firm, crisp, light blue color, and very large size. After two additional years of evaluation in Lowell, Oreg. and Northwest Washington, 'FC13-083' was determined to be sufficiently cold hardy and adaptable to varying soil conditions and commercial management strategies and have a competitive yield for the harvest season. Plants of 'FC13-083' propagated from softwood cuttings or in vitro are phenotypically stable and exhibit the same characteristics as the original plant.

SUMMARY OF THE INVENTION

The new blueberry plant variety 'FC13-083' has not been observed under all possible environmental conditions. The phenotype may vary somewhat with variations in environment and cultural practices such as temperature and light intensity without, however, any variance in genotype.

'FC13-083' is distinguished by an upright growth habit, moderate vigor, yellow fall leaf color, and very large fruit with a light blue color and oblate shape. The following characteristics of the new cultivar have been repeatedly observed and are determined to be the unique characteristics of the new blueberry plant variety 'FC13-083':

1) Early- to mid-season ripening.
2) Very large, uniform fruit size.
3) Very crisp and flavorful fruit.

BRIEF DESCRIPTION OF THE DRAWINGS

The accompanying photographic illustration shows typical specimens in full color of the foliage and fruit of the new variety 'FC13-083'. The colors are as nearly true as is reasonably possible in a color representation of this type.

Figure 1:
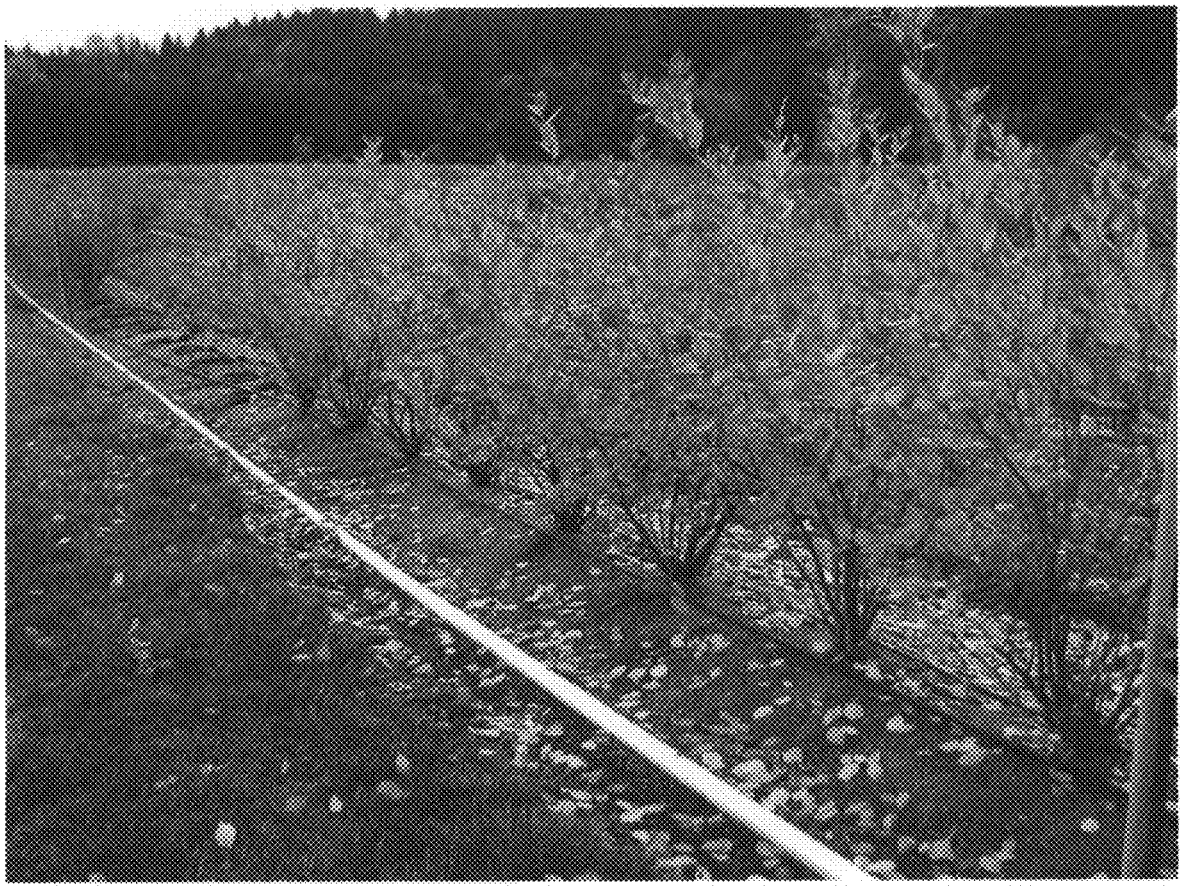
FIG. 1 is a photograph of the new variety 'FC13-083', demonstrating the plant's leaves and growth habit in the fall. The plants were grown in Lowell, Oreg. and photographed on Nov. 15, 2017.
Figure 2:
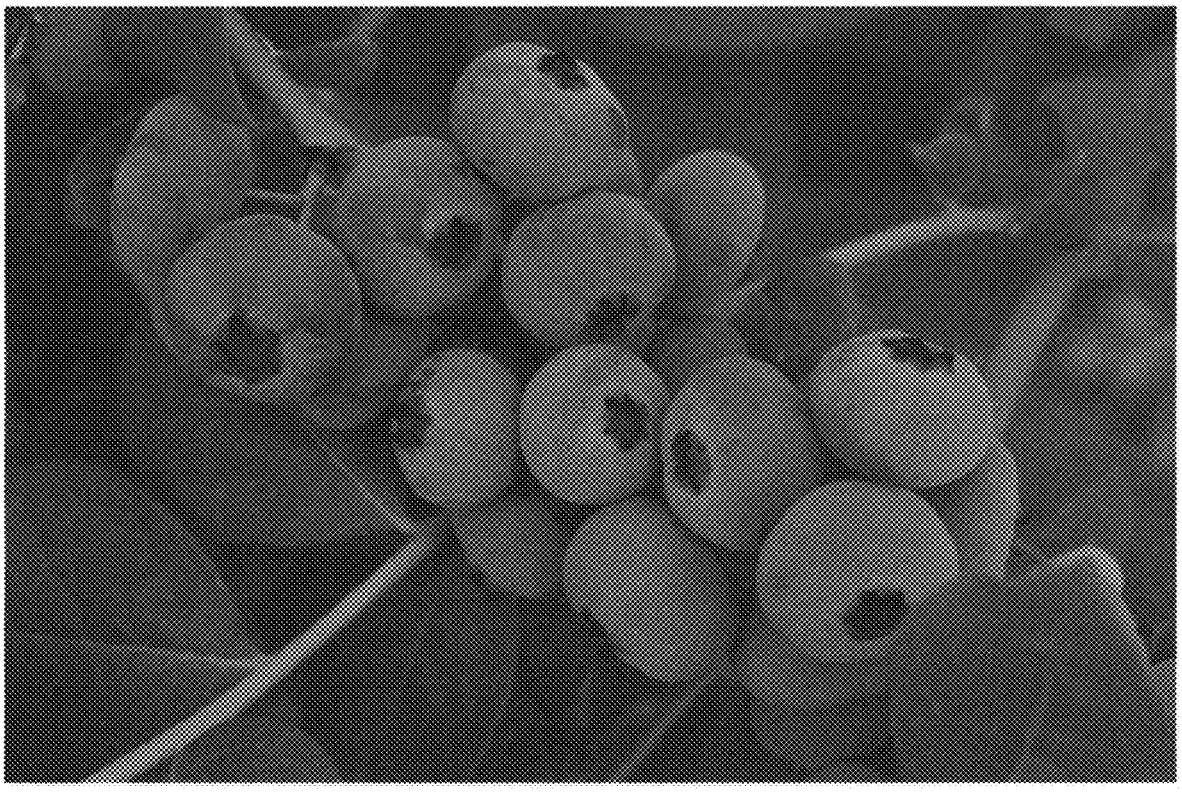
FIG. 2 is a photograph of the fruit cluster of the new variety 'FC13-083' grown in Lowell, Oreg. and photographed on Jul. 11, 2017.
Figure 3:
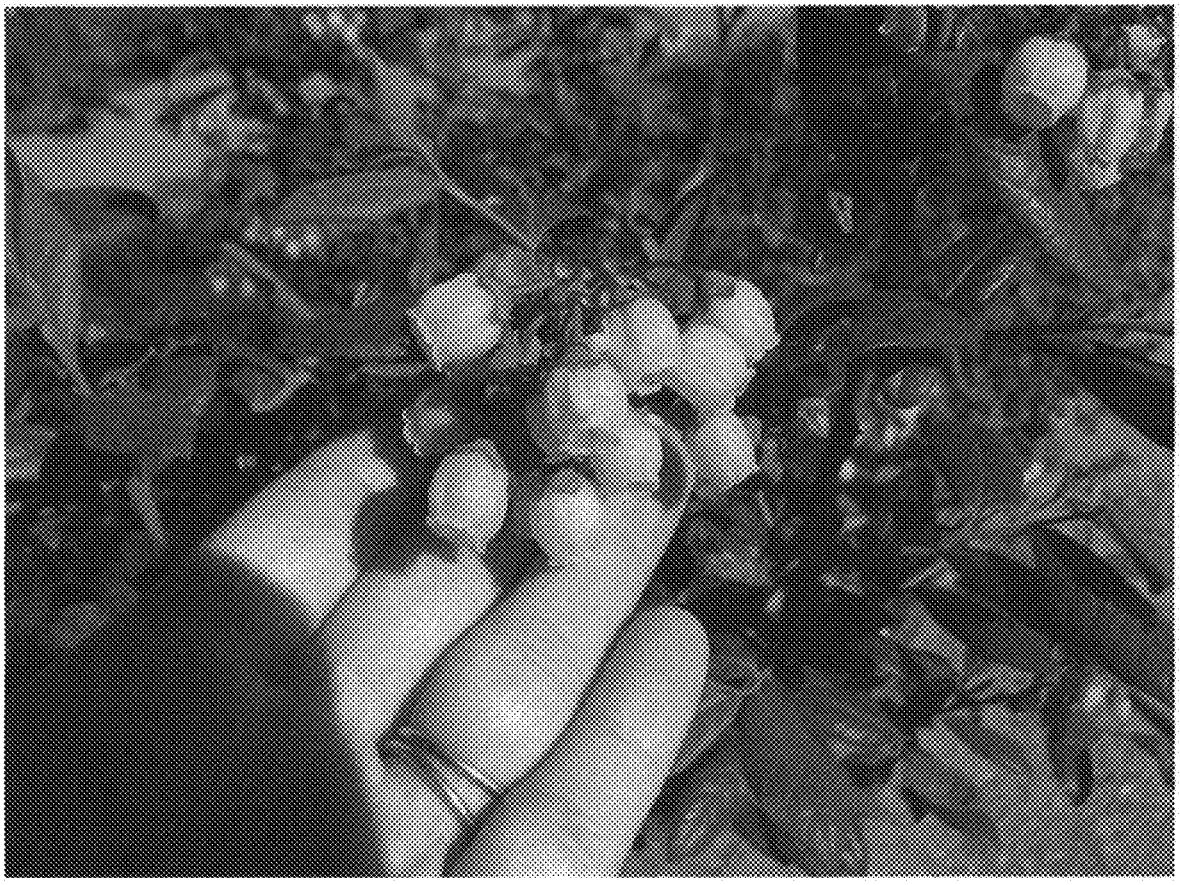
FIG. 3 is a photograph of the flowers of the new variety 'FC13-083' grown in Lowell, Oreg. and photographed on May 4, 2017.
Figure 4:
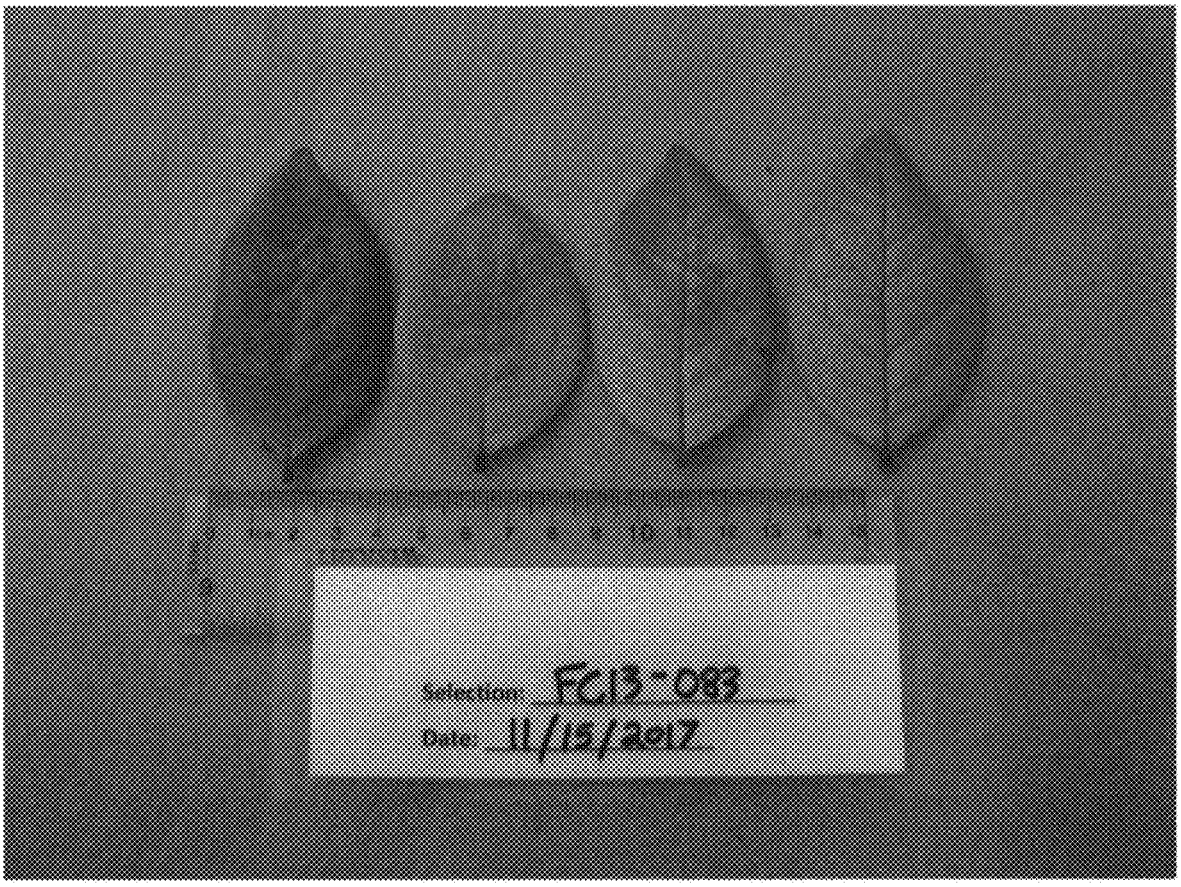
FIG. 4 is a photograph of the fall foliage of the new variety 'FC13-083' grown in Lowell, Oreg. and photographed on Nov. 15, 2017.
Figure 5:
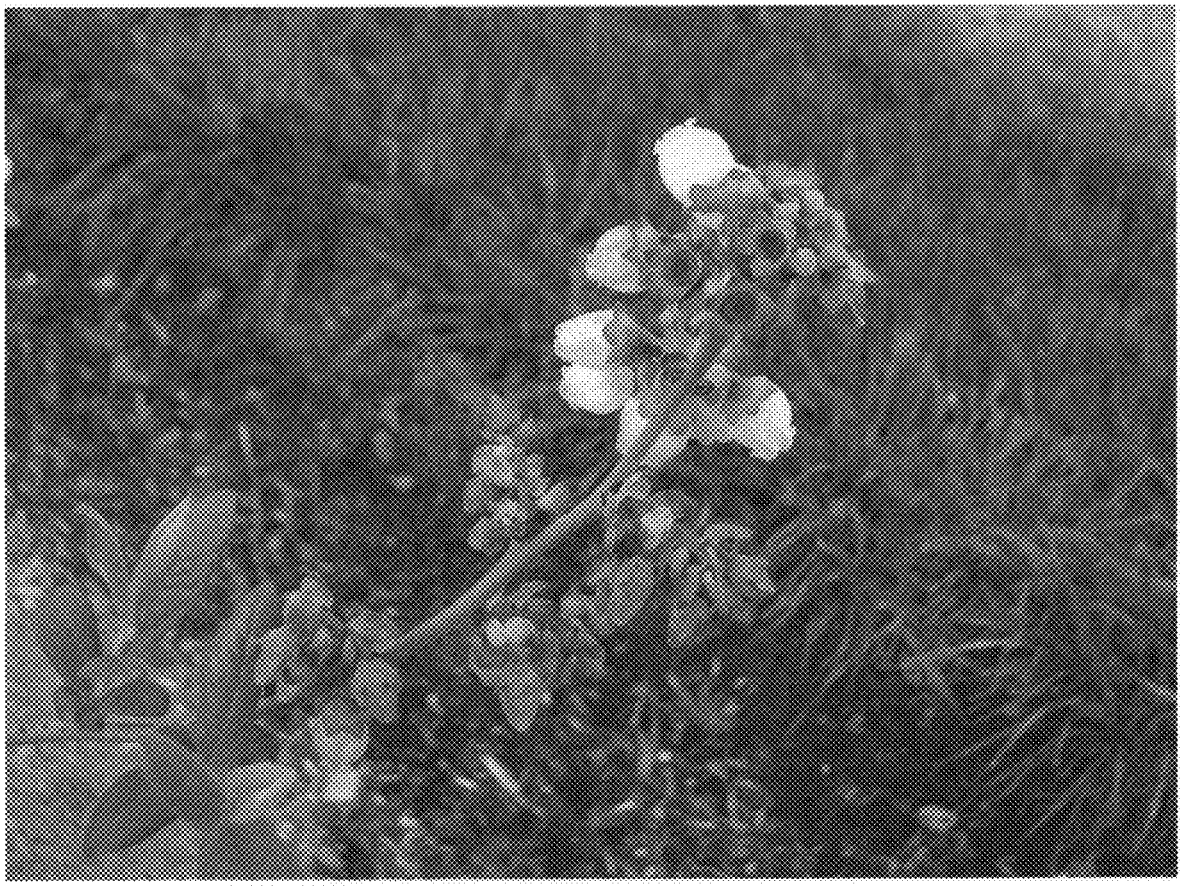
FIG. 5 is a photograph of early buds and flowers on the variety 'FC13-083' grown in Lowell, Oreg. and photographed on Apr. 19, 2017.
Figure 6:
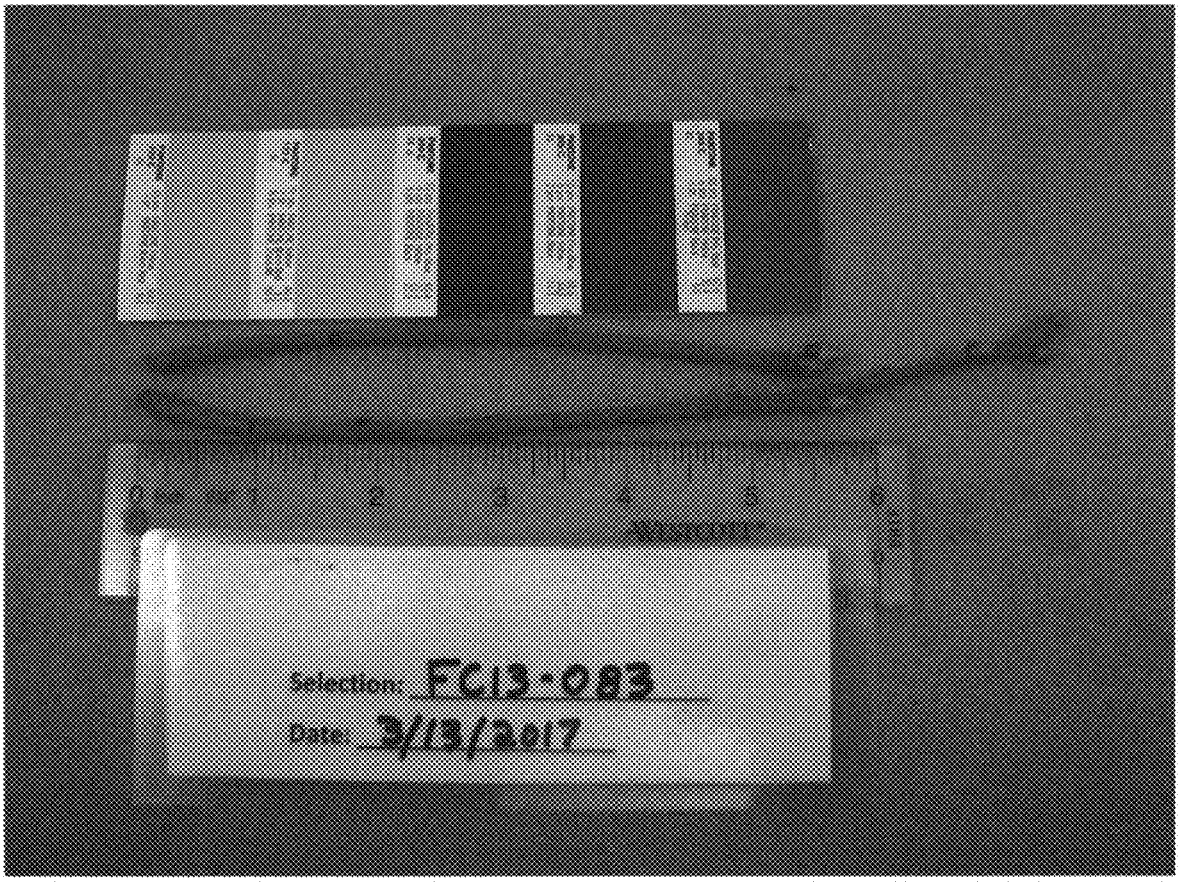
FIG. 6 is a photograph of one year old canes on the variety 'FC13-083' grown in Lowell, Oreg. and photographed on Mar. 13, 2017.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'FC13-083'. The data which define these characteristics were collected from asexual reproductions of the original selection. Dimensions, sizes, colors, and other characteristics are approximations and averages set forth as accurately as possible. The plant history was taken on plants approximately 3 years of age, and the descriptions relate to plants grown in the field located at 39252 Jasper-Lowell Road, Lowell, Oreg., USA. Descriptions of fruit characteristics were made on fruit grown at the field described above. Color designations are from "The Pantone Book of Color" (by Leatrice Eiseman and Lawrence Herbery, Harry N. Abrams, Inc., Publishers, New York 1990) and "R.H.S. Colour Chart, 5$^{th}$ Edition" (Royal Horticulture Society, London 2007). Where the Pantone and R.H.S. color designations differ from the colors of the photographs, the Pantone and R.H.S. colors are accurate.

Classification:

a. *Family*.—Ericaceae.
b. *Genus*.—*Vaccinium*.
c. *Species*.—*Corymbosum*.
d. *Common name*.—Northern Highbush Blueberry.

Parentage: Female Parent — 'ZF06-050.' (not patented).
Male Parent — 'ZF06-013.' (not patented).

Market class: Hand harvest fresh market.

PLANT

General:

a. *Plant height*.—Average 1.39 m.
b. *Plant width*.—Average 1.68 m.
c. *Growth habit*.—Upright.
d. *Growth*.—Moderate vigor.
e. *Productivity*.—High. In Lowell, Oreg. on 2 year old plants 3.26 lbs. per plant, compared to 'Duke' (not patented) plants of the same age which produced an average of 1.81 lbs. per plant. On 3 year old plants 'FC13-083' produced 3.19 lbs. per plant, compared to 'Duke' that produced an average of 2.32 lbs. per plant.
f. *Cold hardiness*.—Approximately USDA zones 6-8 but tested to only USDA zone 8.
g. *Chilling requirement*.—Estimated minimum of 500-1000 hours below 45 degrees Fahrenheit.
h. *Leafing*.—Moderate.
i. *Twigginess*.—Not twiggy.
j. *Resistance/susceptibility to root rot* (*phytopthora cinnamomii*).—Does not seem overly susceptible.
k. *Resistance/susceptibility to stem blight* (*botryosphaeria sp.*).—Does not seem overly susceptible.
l. *Resistance/susceptibility to phomopsis twig blight* (*phomopsis vaccinii*).—Does not seem overly susceptible.
m. *Resistance/susceptibility to botrytis* (*botrytis cinerea*).—Does not seem overly susceptible.
n. *Resistance/susceptibility to leaf spot* (*Septoria spp.*) .—Does not seem overly susceptible.
o. *Resistance/susceptibility to leaf rust* (*Naohidemyces vaccinii*).—Does not seem overly susceptible.
p. *Resistance/susceptibility to bud mites* (*acalatus vaccinii*).—Undetermined.

STEM

General:

a. *Suckering tendency*.—None.
b. *Mature cane color*.—Pantone color Glaze Ginger 18-1154.
c. *Mature cane length*.—Average 1.34 m.
d. *Mature cane width*.—Average 1.41 cm.
e. *Bark texture*.—Rough.
f. *Fall color on new shoots*.—Pantone color Chive 19-0323.
g. *Surface texture of new wood*.—Smooth.
h. *Internode length on strong, new shoots*.—28.21 mm.
i. *Average number of buds per fruiting lateral*.—6.4.

FOLIAGE:

General:

a. *Time of beginning of leaf bud burst*.—In Lowell, Oreg., early to late March.
b. *Leaf color* (*top side*).—RHS 139A.
c. *Leaf color* (*under side*).—RHS N138C.
d. *Leaf arrangement*.—Alternate and spirally arranged: dextrose.
e. *Leaf shape*.—Broadly elliptic.
f. *Leaf margins*.—Entire.
g. *Undulation of margin*.—None.
h. *Leaf venation*.—Reticulate.

i. *Leaf apices*.—Acute.
j. *Leaf bases*.—Obtuse.
k. *Leaf length*.—Average 67.54 mm.
l. *Leaf width*.—Average 38.71 mm.
m. *Leaf length/width ratio*.—1.75 — medium.
n. *Leaf nectarines*.—Absent.
o. *Pubescence of upper side*.—None.
p. *Pubescence of lower side*.—None.
q. *Cross sectional profile*.—Flat.
r. *Longitudinal profile*.—Plane.
s. *Attitude*.—Porrect.
t. *Fall leaf color*.—Pantone color Maize 13-0746 and Pantone color Chive 0323.

Petioles:
a. *Length*.—Average 3.56 mm.
b. *Width*.—Average 2.11 mm.
c. *Color*.—Pantone color Pink Sand 15-1318 and Pantone color Celery Green 13-0532.
d. *Petiole surface texture*.—Smooth.

FLOWERS

General:
a. *Time of beginning of flowering*.—Approximately mid-April in Lowell, Oreg.
b. *Time of* 50% *anthesis*.—Approximately early May in Lowell, Oreg.
c. *Flower shape*.—Urceolate.
d. *Flower bud density*.—Medium.
e. *Flower fragrance*.—Faint floral scent.
f. *Immature flower color*.—Pantone color Pastel Parchment 11-0603.

Corolla:
a. *Color*.—Pantone color Snow White 11-0602.
b. *Length*.—8.84 mm.
c. *Width*.—9.10 mm.
d. *Aperture width*.—5.20 mm.
e. *Anthocyanin coloration of corolla*.—Very low to none.
f. *Corolla ridges*.—Present.
g. *Protrusion of stigma*.—0.00 — does not protrude, level with corolla.

Inflorescence:
a. *Length*.—32.62 mm.
b. *Diameter*.—33.88 mm.
c. *Length of peduncle*.—17.24 mm.
d. *Surface texture of peduncle*.—Smooth.
e. *Color of peduncle*.—Pantone color Rosewood 19-1532.
f. *Length of pedicel*.—7.10 mm.
g. *Surface texture of pedicel*.—Smooth.
h. *Color of pedicel*.—Pantone Color Rosewood 19-1532.
i. *Number of flowers per cluster*.—6.8.
j. *Flower cluster density*.—Medium.

Calyx (with sepals):
a. *Diameter*.—9.78 mm.
b. *Color* (*sepals*).—Pantone color Jade Lime 14-0232.

Stamen:
a. *Length*.—6.38 mm.
b. *Number per flower*.—12 stamen per flower.
c. *Filament color*.—Pantone color Green Glow 13-0442.

Pistil:
a. *Length*.—11.55 mm.
b. *Ovary color* (*exterior*).—Pantone color Parrot Green 15-0341.
c. *Style length*.—8.28 mm.

Anther:
a. *Length*.—3.55 mm.
b. *Number*.—2 anthers per stamen.
c. *Color*.—Pantone color Metal Bronze 17-0992.

Pollen:
a. *Abundance*.—Moderate.
b. *Color*.—Pantone color Cornhusk 12-0817.

FRUIT

General:
a. *Time of fruit ripening*.—Approximately May to July in Lowell, Oreg.
b. *Time of* 50% *maturity*.—Approximately the beginning of July in Lowell, Oreg.
c. *Fruit development period*.—59 days in Lowell, Oreg. in 2017.
d. *Mean harvest date*.—July 4.
e. *Mean date last pick*.—July 11.
f. *Cluster density*.—Medium-dense.
g. *Berries per cluster*.—5.2 berries per cluster.
h. *Unripe fruit color*.—Pantone color Bright Chartreuse 14-0445.
i. *Ripe berry color*.—RHS 98C.
j. *Berry skin color after polishing*.—RHS 103A.
k. *Berry surface wax abundance*.—Medium.
l. *Berry flesh color*.—Pantone color Hay 12-0418.
m. *Berry weight*.—Average 3.90 g.
n. *Berry height from calyx to scar*.—15.37 mm.
o. *Berry diameter*.—22.91 mm.
p. *Calyx aperture*.—Average 6.74 mm.
q. *Calyx depth*.—Average 1.07 mm.
r. *Pedicel length*.—Average 10.66 mm.
s. *Pedicel surface texture*.—Smooth.
t. *Berry detachment force*.—Medium.
u. *Berry shape*.—Slightly oblate.
v. *Fruit stem scar*.—Small, dry.
w. *Sweetness when ripe*.—High.
x. *Firmness when ripe*.—High.
y. *Acidity when ripe*.—Low.
z. *Storage quality*.—Excellent.

SEED

General:
a. *Seed abundance in fruit*.—Moderate.
b. *Seed color*.—Pantone color Brown Sugar 17-1134.
c. *Seed dry weight*.—0.27 mg. per seed.
d. *Seed length*.—Average 1.58 mm.

COMPARISON BETWEEN PARENTAL AND COMMERCIAL CULTIVARS

TABLE 1

Comparison Table

| Denomination of similar variety | Characteristic for comparison | State of expression of similar variety | State of expression of candidate variety 'FC13-083' |
|---|---|---|---|
| Duke | Fruit size | 2.33 g. (Large) | 3.95 g. (Very large) |
| Draper (U.S. Plant Pat. No. PP15,103) | Fruit size | 2.53 g. (Large) | 3.95 g. (Very Large) |
| Duke | Mean harvest date | Early | Early-Mid (one week after Duke) |

TABLE 1-continued

Comparison Table

| Denomination of similar variety | Characteristic for comparison | State of expression of similar variety | State of expression of candidate variety 'FC13-083' |
|---|---|---|---|
| Draper | Fruit firmness at 14 days cold storage | 250 g./mm. | 420 g./mm. |
| Duke | Fall leaf color | Reddish orange | Yellow and green |
| ZF06-050 | Vigor | Low | Moderate |
| ZF06-013 | Growth habit | Semi-sprawl | Upright |

The invention claimed is:

1. A new and distinct variety of blueberry plant named 'FC13-083', substantially as illustrated and described herein.

* * * * *